(12) United States Patent
Cerundolo et al.

(10) Patent No.: US 11,147,567 B2
(45) Date of Patent: Oct. 19, 2021

(54) METHODS AND DEVICES FOR RESTORATION OF A BONE SURFACE

(71) Applicant: Joint Restoration Foundation, Inc., Centennial, CO (US)

(72) Inventors: Daniel Cerundolo, Hingham, MA (US); Keith Byers, Denver, CO (US); Matthew Provencher, Avon, CO (US); Matthew Fretzs, Littleton, CO (US)

(73) Assignee: Joint Restoration Foundation, Inc., Centennial, CO (US)

( * ) Notice: Subject to any disclaimer, the term of this patent is extended or adjusted under 35 U.S.C. 154(b) by 208 days.

(21) Appl. No.: 16/287,992

(22) Filed: Feb. 27, 2019

(65) Prior Publication Data

US 2019/0262010 A1  Aug. 29, 2019

Related U.S. Application Data (60) Provisional application No. 62/636,651, filed on Feb. 28, 2018.

(51) Int. Cl.
| | |
|---|---|
| *A61B 17/16* | (2006.01) |
| *A61F 2/46* | (2006.01) |
| *A61B 17/15* | (2006.01) |
| *A61F 2/30* | (2006.01) |

(52) U.S. Cl.
CPC .......... *A61B 17/1635* (2013.01); *A61B 17/15* (2013.01); *A61F 2/4644* (2013.01); *A61F 2002/30766* (2013.01)

(58) Field of Classification Search
CPC . A61B 17/15; A61B 17/1635; A61B 17/8863; A61F 2/4644; A61F 2002/4649; A61F 2002/30766; A61F 2002/2835; A61F 2002/2839
See application file for complete search history.

(56) References Cited

U.S. PATENT DOCUMENTS

| | | | |
|---|---|---|---|
| 6,409,730 B1 | 6/2002 | Green et al. | |
| 6,440,444 B2 | 8/2002 | Boyce et al. | |
| 7,828,853 B2 | 11/2010 | Ek et al. | |
| 8,475,462 B2 * | 7/2013 | Thomas | A61B 17/15 606/87 |

(Continued)

OTHER PUBLICATIONS

Bugbee et al., "Bipolar Fresh Osteochondral Allografting of the Tibiotalar Joint," *The Journal of Bone & Joint Surgery*, vol. 95-A, No. 5, Mar. 6, 2013, pp. 426-432.

(Continued)

*Primary Examiner* — Anu Ramana
(74) *Attorney, Agent, or Firm* — Brownstein Hyatt Farber Schreck, LLP (57) ABSTRACT

Instrumentation sets and methods for preparing and implanting an osteochondral allograft to a bone lesion. Instrumentation sets include a pair of guide blocks, a recipient guide block and an allograft guide block, for preparing a cavity at the bone lesion matched by a similarly sized and shaped allograft. Guide blocks provide simple and direct techniques for preparing a matching cavity, formed at the bone lesion, to a bone implant, to be secured within the cavity. Methods include use of the instrumentation to restore bone surfaces for any number of sites using any allograft source. In some cases, the bone lesion is in a humeral head and the allograft source is a talus.

21 Claims, 11 Drawing Sheets

(56) References Cited

U.S. PATENT DOCUMENTS

| | | | |
|---|---|---|---|
| 8,523,864 B2* | 9/2013 | Malinin | A61F 2/4644 |
| | | | 606/79 |
| 8,597,362 B2 | 12/2013 | Shenoy et al. | |
| 8,679,123 B2 | 3/2014 | Kinmon et al. | |
| 8,690,956 B2 | 4/2014 | Cook et al. | |
| 9,370,428 B2 | 6/2016 | Winslow et al. | |
| 9,622,871 B2 | 4/2017 | Sander | |
| 2007/0207185 A1* | 9/2007 | Hart | A61P 19/08 |
| | | | 424/423 |
| 2010/0318088 A1* | 12/2010 | Warne | A61B 17/15 |
| | | | 606/87 |
| 2011/0257756 A1 | 10/2011 | Strzepa et al. | |
| 2014/0350688 A1 | 11/2014 | Michel et al. | |
| 2015/0297361 A1* | 10/2015 | Kehres | B25B 5/147 |
| | | | 83/13 |

OTHER PUBLICATIONS

Bugbee et al., "Osteochondral Allograft Transplantation in Cartilage Repair: Graft Storage Paradigm, Translational Models, and Clinical Applications," Journal of Orthopaedic Research, Jan. 2016, pp. 31-38.
Makino et al., "The Effect of Graft Sizing on Osteochondral Transplantation," *Arthroscopy*, Oct. 2004, 20:8, pp. 837-840.
U.S. Appl. No. 16/002,662, filed Jun. 7, 2018, Mologne et al.
U.S. Appl. No. 16/252,331, filed Jan. 18, 2019, Tabbaa et al.

* cited by examiner

METHODS AND DEVICES FOR RESTORATION OF A BONE SURFACE

CROSS-REFERENCE TO RELATED APPLICATION

This application claims the benefit under 35 U.S.C. § 119(e) to U.S. Provisional Patent Application No. 62/636,651, filed Feb. 28, 2018, the contents of which are incorporated herein by reference as if fully disclosed herein.

TECHNICAL FIELD

The present invention relates to osteochondral allograft implant instruments and procedures, and more particularly, to methods and devices for transplanting an osteochondral allograft to a damaged bone lesion.

BACKGROUND OF THE INVENTION

Bone defects can result from a number of causative events, for example, infection, cancer, and inflammation can lead to serious processes that result in loss of vital bone tissue. In addition, trauma to bone via fracture or joint damage often results in defects that require clinical intervention. In the absence of clinical intervention, bone defects can lead to serious complications like arthritis and secondary infection, as well as to the loss or reduction of bone or joint function. A typical type of clinical intervention involves bone transplantation.

Bone transplantation to correct bone defects in a recipient is a fairly common surgical procedure. Transplantation typically involves removing a circular bone plug from a source of bone (either an autograft or an allograft) and filling the recipient's bone defect to encourage proper healing. Small bone defects may be targeted with autograft plugs, while more significant defects typically require allograft tissue. Clinicians typically prepare a bone plug using transplant techniques that rely predominately on the clinicians know-how and non-specialized surgical tools. Where specialized tools have been developed, fairly complex instrumentation has been proposed, such that costs, time and education of the process makes the solutions difficult to implement.

Failure to successfully treat a bone defect can result in impairment of the bone or joint function, increased pain, bone necrosis, infection, arthritis, and other negative outcomes.

The present invention is directed toward overcoming one or more of the problems discussed above.

SUMMARY OF THE INVENTION

This disclosure details surgical instrumentation and related techniques for restoring bone surfaces to a damaged bone. The embodiments herein are used to size and shape an allograft to a matching site in a damaged bone. The implantation of the allograft reconstructs the damaged bone for proper healing. Embodiments herein move away from conventional osteochondral transplantation techniques which have predominately utilized circular or oval shaped implants. As will be described herein, the majority of damaged bone that require restoration of the bone surface, particularly defects like Hill-Sachs and Reverse Hill-Sachs, would greatly benefit from wedge or rectangular shaped implants. Embodiments herein provide this significant improvement in treatment over the conventional techniques.

In one embodiment, an instrumentation set for restoration of a bone lesion is provided. The instrumentation set includes a recipient guide block and an allograft guide block. The recipient guide block is configured to be secured against the surface of the bone lesion so as to guide a user in the preparation of a predetermined sized and shaped cavity, typically having a wedge, rectangular or non-circular shape. The allograft guide block is configured to be secured against the surface of an allograft source to guide the user in the preparation of a predetermined sized and shaped allograft or implant. The predetermined sized and shaped allograft is secured in the predetermined sized and shaped cavity to restore the surface of the bone lesion. In some aspects, the recipient guide block and allograft guide block are both configured to directly attach to the bone lesion or allograft source, respectively. In other aspects, the recipient guide block and allograft guide block are each positioned relative to the bone lesion and allograft source via a scaffold fixture, respectively. In some aspects the bone lesion is located in a humeral head and the allograft source is a talus bone.

In other aspects of the disclosed embodiments, the recipient guide block has a top surface and an opposing bottom surface, where a uniform thickness extends between the top and bottom surfaces. In addition, the recipient guide block can have a centerline with at least two holes along the centerline configured to accept screws or pins to attach the recipient guide block to the bone lesion. The recipient guide block may also define at least a first cutting slot at a first distance from the centerline, and at least a second cutting slot at a second distance from the centerline, the first and second distances being substantially equal. In typical embodiments, the cutting slots are configured to allow a user to make angled cuts along either side of the bone lesion.

In still other aspects of the disclosed embodiments, the allograft guide block has a top surface and an opposing bottom surface, where a uniform thickness extends between the top and bottom surfaces. In addition, the allograft guide block can have a centerline with at least two holes on a first side of the centerline, and at least two holes on the opposing side of the centerline, where each hole is configured to accept screws or pins to attach the allograft guide block to an allograft source (bone source). Attachment of the allograft guide block to the allograft source is such that the allograft is not damaged through guide block attachment. As with the recipient guide block, the allograft guide block may define at least a first cutting slot at a first distance from the centerline, and at least a second cutting slot at a second distance from the centerline, the first and second distances being substantially equal. The distance between the first and second cutting slot are configured to match the distances between cutting slots in the recipient guide block, thereby providing similarly sized and shaped cavities and implants/allografts. In some aspects, the distance between the first and second guide block takes into account the width of the cutting device used to remove the allograft. In other aspects, the radius of contour of the allograft source is substantially the same as the radius of contour for the recipient bone under restoration.

In other aspects of the disclosed embodiments, a scaffolding fixture has a vice that fixes an allograft source for allograft production in position. A movable post is associated, directly or indirectly, with the fixed-in place allograft source. The movable post is capable of being moved to a position adjacent the harvest site for the allograft. In this embodiment, an allograft guide block is configured to attach to a top end of the post and extend above the surface of the allograft source at any desired angle. The post can be raised or dropped or rotated clockwise or counter-clockwise to a level and position that facilitates placement of the guide block above the allograft source surface. The guide block—post assembly secures the defined cutting slots above the allograft source as has been previously described for the other guide block embodiments. However, unlike other embodiments, the allograft guide block does not require direct attachment to the allograft source surface, rather, is simply positioned above the surface using the movable post and avoids use of pins or screws to secure the guide block to the allograft source.

In other embodiments, a method is disclosed for restoring a bone surface, the method including the steps of: obtaining a donor bone as an allograft source; securing a recipient guide block against the surface of a bone lesion and using the recipient guide block to cut out the bone lesion and prepare a predetermined sized and shaped cavity; securing an allograft guide block against the surface of the allograft source to prepare a predetermined sized and shaped allograft that has the same size and shape as the recipient cavity; and securing the allograft into the recipient bone cavity.

In aspects of the method, a radius of contour for an exterior surface of the donor bone is similar to a radius of contour for the surface of the recipient's bone surface. In addition, the securing of the allograft guide block to the donor bone is through the use of at least four sidecar pins or screws. Methods herein also include that the cut out of the recipient lesion is accomplished using a cutting blade guided by two or more angled cutting slots defined in the recipient guide block. In some cases, the defined angled cutting slots run parallel to each other. Defined angled cutting slots can be configured to be at any angle with reference to the top and bottom surfaces of the guide blocks.

In yet another embodiment herein, a method for restoring a bone surface is provided, including: obtaining a donor bone as an allograft source; securing a recipient guide block directly against the surface of a recipient lesion and using the recipient guide block to cut out the recipient lesion and prepare a predetermined sized and shaped cavity; securing an allograft guide block directly against the donor bone to prepare a predetermined sized and shaped implant that has the same size and shape as the recipient cavity; and securing the implant into the cavity.

In still other embodiments herein, a kit for restoring a bone surface is provided. The kit including a recipient guide block configured to be secured directly against a lesion and to guide preparation of a wedge shaped cavity at the lesion; an allograft guide block configured to be secured directly against an allograft source and to guide preparation of a wedge shaped implant or allograft for positioning in the cavity; and instructions on how to utilize the recipient guide block and allograft guide block to repair the lesion in the bone. In aspects herein, the kit also includes screws or pins for use in securing the recipient and allograft guide blocks to the bone lesion or allograft source, respectively. Aspects of the kit can also include an allograft source, and in some cases a talus bone as the allograft source. In other aspects, the kit can include a scaffolding fixture for positioning of a configured allograft guide block above the surface of an allograft source for allograft production.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

Before proceeding with the detailed description, it is to be appreciated that the present teaching is by way of example only, not by limitation. The concepts herein are not limited to use or application with a specific system or method for restoration of a humeral head bone defect.

The present disclosure relates to device, kit and method embodiments used to repair bone defects in a damaged bone surface. Repair of the bone surface using the embodiments herein facilitates proper healing and function of the bone, as well as results in a potential reduction in healing time for the patient. Embodiments herein provide for the preparation of non-circular allograft implants, i.e., wedge shaped, rectangular shaped, square shaped, etc., that can be tailored for snug fits into a damaged bone defect (a significant improvement over conventional techniques that produce circular shaped implants). Where a joint is involved (knee, elbow, shoulder, etc.), repair of the bone improves joint stability and function. In addition, embodiments herein allow for a more efficient surgical procedure in regard to the use of allograft source material, as well as to the amount of time the surgeon requires to obtain a matching allograft for a targeted defect. The embodiments herein are disclosed for use in resurfacing a damaged bone, in particular, aspects herein can be used wherever there is a need for a sized and shaped allograft for a damaged shoulder, elbow, knee, foot, ankle, hip and the like. In one illustrative aspect, embodiments herein can be described in relation to resurfacing a damaged humeral head.

Embodiments herein relate to transplanting correctly sized, shaped and surface contoured osteoarticular allografts to defects in a bone. In one embodiment, the defect is located in a humeral head, in another embodiment, the defect is located in a tibia, in still another embodiment, the defect is located in the ulnar, and in still another embodiment, the defect is located in the talus, for example. For purposes herein, an allograft is a bone implant from a donor source of the same species as the recipient, but is not genetically identical. For clarity, an autograft is a graft of tissue from a first point to a second point of the same individual's body.

In general, in accordance with embodiments herein, a sized and surface contoured allograft bone source is prepared and secured within a size and shape matched cavity previously or contemporaneously prepared at a lesion site. Preparation of the implants and bone lesion cavity herein are accomplished through the use of a pair of guide blocks, where the guide blocks allow for matching size and shape cutting patterns to be prepared in an implant, and corresponding bone lesion cavity, and require little or no other preparation in their use. As such, the guide blocks herein are a significant improvement over existing methodology as they provide a simple and straightforward solution for bone transplantation.

As such, embodiments herein utilize a pair of guide blocks, a recipient guide block for guiding the removal of tissue from the patient's lesion, and an allograft guide block for preparing an allograft from an osteochondral allograft source having the same dimensions as the cavity prepared at the patient's lesion. The two guide blocks utilize cutting slots oriented off of a centerline to provide for the same size cavity in the lesion as allograft prepared to be placed in the lesion. In some aspects, the cavity size and allograft implant take into account the width of the cutting blade to ensure a snug fit. As will be more fully described herein, proper 3D surface contour of the implanted allograft is provided by the source of allograft, where the radius of curvature of the donor bone roughly matches the native curvature of the recipient bone. As such, the implant size, shape and surface contour can substantially match the damaged bone and allow for an efficient resurfacing of the bone.

In one embodiment, guide blocks are square or rectangular in shape, and have two relatively flat surfaces separated by a uniform thickness (other shapes and sizes are contemplated for the guide blocks, as long as the blocks function according to embodiments herein). Edges of the guide blocks can meet at a point, typically at a right angle, or can form rounded edges. In typical aspects, the guide blocks are of sufficient size to attach to and fully cover a bone lesion and corresponding allograft source implant harvest site. In one embodiment the guide blocks are square or rectangular and roughly 40 mm to 70 mm×40 mm to 70 mm. In another embodiment, the guide blocks are 50 mm to 60 mm×50 mm to 60 mm, and is some embodiments, the guide blocks most typically 50 mm×50 mm, and have a uniform thickness between a top and bottom surface of between 4-7 mm, more typically 5-6 mm, and most typically about 5 mm. One embodiment includes guide blocks that are each roughly 50 mm×50 mm in dimension, having an uniform thickness between surfaces of approximately 5 mm. A typical guide block is made of stainless steel or stainless steel alloy. Guide blocks can be reusable upon sterilization, or be disposed of after a single use. In some aspects, these guide blocks are rigid and maintain their integrity over a number of sterilization and uses. Other materials are also contemplated for preparation of guide blocks, for example, guide blocks can also be prepared from various plastics, like, acetal copolymer, high-density polyethylene, polycarbonate, polyethermide, and the like. In some aspects, the guide blocks can maintain limited flexibility, to facilitate limited molding along the contour of a bone surface. Plastic guide blocks may also be sterilized under proper conditions or be disposable after a single use.

It is also envisioned that guide blocks can have an overall concave shape, such that the guide blocks top and bottom surfaces are inwardly curved to substantially match the curvature of the underlying recipient or donor bone surface. Each pair of guide blocks can have the same inward curvature, and a series of guide block pairs can be manufactured, each having a different curvature to accommodate different sized recipient and donor bones.

Allograft guide blocks in accordance with embodiments herein can be directly attached and positioned to an allograft, or can be positioned relative to the allograft using a scaffolding fixture. Typical scaffolding fixtures include a vice to secure the allograft source, and movable post, relative to the vice, the post having a guide block attached thereto. The post and guide block being configured to position the guide block above the surface of the allograft source. In these embodiments, where placement is through scaffolding, the allograft guide block can have a uniform thickness of from about 3 mm to about 8 mm, and include an attachment means for operative attachment to the post of the scaffolding.

Embodiments herein will now be described in relation to a bone lesion in a humeral head using an allograft source of a talus, or an allograft source of a humeral head. Note that this is for illustrative purposes only and not meant to limit the scope of the invention. Embodiments herein cover all potential bone lesion sites and use of any sufficiently sized and surfaced donor bone sources.

As such, in one embodiment herein, the sized and surface contoured allograft bone source is from a talus, and the matched cavity lesion site is in a humeral head. In another aspect, the sized and surface contoured allograft bone source is from a humeral head and the matched cavity lesion site is in a humeral head. Once prepared using embodiments herein, the talus or humeral head derived allograft is secured in the cavity defect so as to have matching size, shape and surface contour.

Use of talus osteoarticular bone was identified by the inventors herein for reconstruction of the humeral head based on its load bearing strength, cartilage surface area coverage, and the talus's unique 3D surface contour. The inventors identified that talus bone has a contour surface that roughly matches the surface contour of a humeral head and therefore is an excellent source of allograft material for glenoid reconstruction. As such, talus bone now represents a new allograft source for glenoid reconstruction.

Use of the humeral head as an osteoarticular source material was identified by the inventors herein based on its anatomical match to the site of defect. Embodiments allow for a targeted removal of allograft from a humeral head that can be size and shape matched to the site of the patient's humeral head defect while matching the 3D surface contour. In general, the surgeon or other health care professional can substantially match the implant source on the humeral head to the site of defect to substantially match the implant contour surface to the defect surface.

Fresh allografts for use in transplantation have a limited shelf life (typically 14-42 days, more typically 21-35 days). The present disclosure provides for a more expanded source of tissue for allograft use during bone surface reconstruction, as well as a more efficient use of the sources, where a surgeon will only require one attempt at preparing the properly sized, shaped and surfaced implant for a particular defect. In addition, talus bone was previously used almost exclusively in ankle or talus reconstruction. Embodiments herein allow for talus as an allograft source in humeral head reconstruction, a significant increase in utility. This increased efficiency, and sourcing, better utilizes the limited resources of allograft materials available for surgeries in the United States and abroad. It is also noted, that even where frozen allograft is used as a source, more efficient and expanded source use for bone reconstruction, is a positive development in bone transplantation.

Embodiments herein will be more fully described with reference to FIGS. 1-15.

Figure 1A:
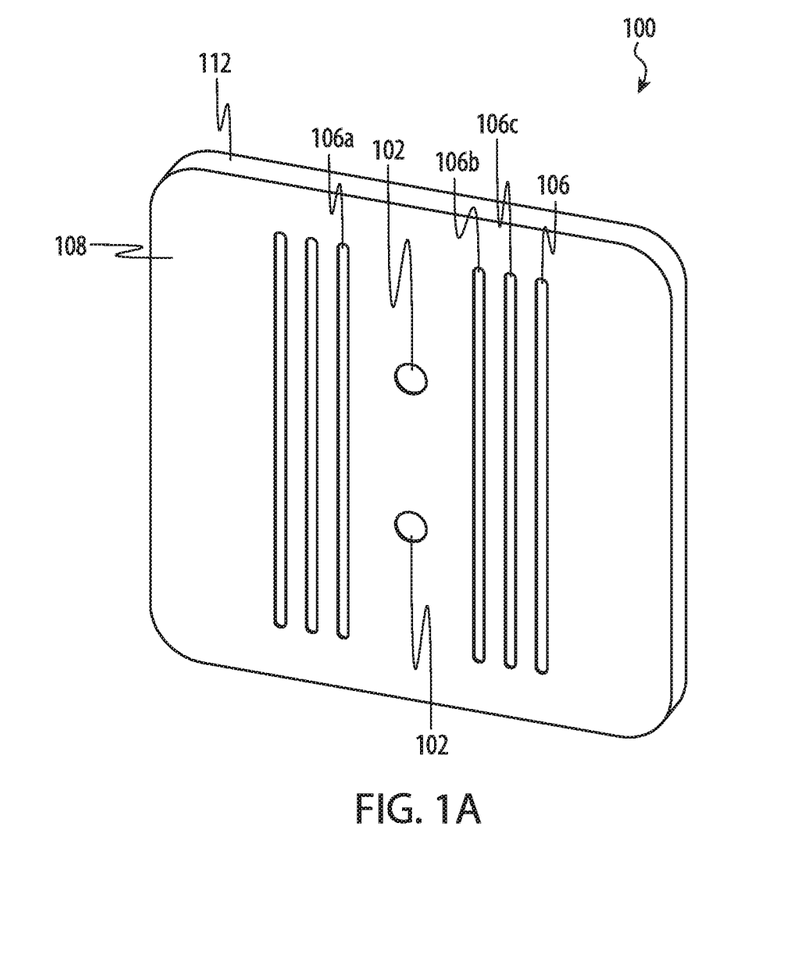
FIG. 1A schematically illustrates a recipient guide block in accordance with embodiments herein.
Figure 1B:
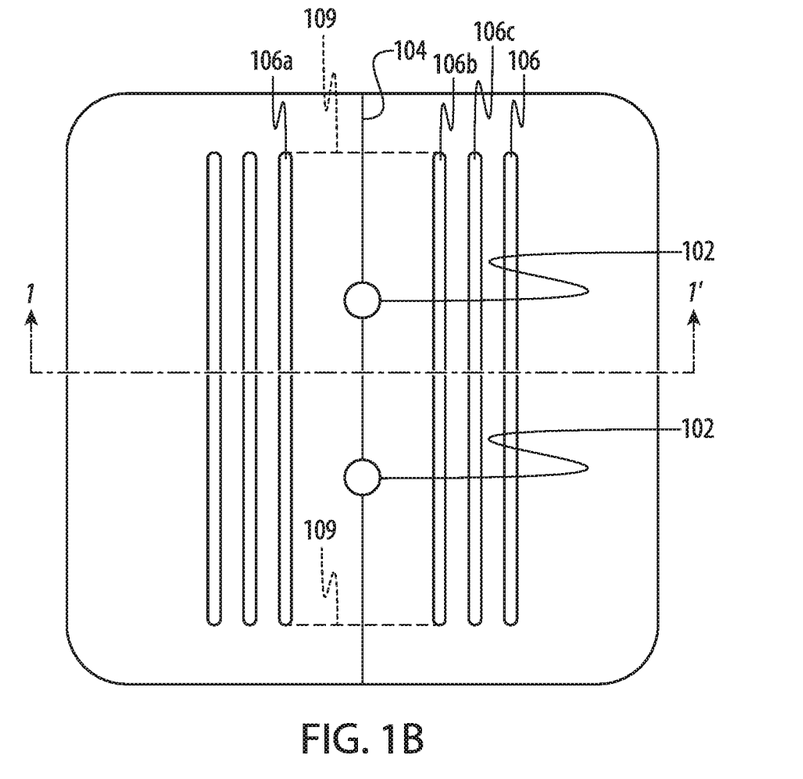
FIG. 1B is a top view of the recipient guide block in accordance with embodiments herein.

FIGS. 1A and 1B show a perspective and top view, respectively, of a recipient guide block 100 in accordance with embodiments herein. The recipient guide block includes at least one center hole, and more typically two center holes 102, for receipt of anchoring pins or screws (not shown), through which the recipient guide block is secured to the underlying bone defect. The recipient guide block is typically square or other like shape, having a uniform thickness, as was described above.

As shown in FIGS. 1A and 1B, the location of the two center holes 102 are aligned along or adjacent a centerline (shown as line 104 in FIG. 1B) of the guide block and, when attached through the center holes, stably fixes the guide block onto a lesion. Note that where the attachment of the guide block 100 to the lesion is through the use of screws, the center holes are appropriately threaded. Once the anchoring pins or screws are adjusted to anchor the recipient guide block to the lesion, a flat bottom surface of the recipient guide block is seated, typically directly, on and over the lesion, while the anchor pins or screws are of sufficient length to rest on or above the opposing flat surface (top) of the recipient guide block, to snugly hold the block in place.

One or more paired cutting slots 106 are defined at proximal to distal intervals from the centerline 104, each cutting slot paired to a cutting slot positioned on the opposite side of the centerline. Cutting slots 106 can be positioned at any useful distance off of the centerline, but are typically positioned at 10 mm as measured from either side of the centerline, 15 mm off of the centerline, and 20 mm off of the centerline, for example. Each cutting slot is roughly parallel to the centerline and to its paired member. Cutting slots are typically of a length to provide the surgeon (or other health care professional) with a guide to cut along the entire length of a lesion, for example, 30 mm in length, 35 mm in length, 40 mm in length, and the like. As such, a first cutting slot 106a is paired to a second cutting slot 106b positioned at equal distances from the guide block centerline 104. In this way the first and second cutting slots are matched to each other. As such, the first and second cutting slots are typically substantially parallel to each other, and extend along at least the entire length of a lesion. As can be imagined, the dimensions of the guide blocks can be configured to host different length cutting slots. For example, a set of smaller guide blocks, perhaps 50 mm×50 mm in dimensions, can define shorter length cutting slots, for example 30 mm in length, where the defect is of a smaller size, compared to a set of larger guide blocks, perhaps 70 mm×70 mm in dimension, where longer length cutting slots are required, for example, 50 mm in length. As such, a series of different sized guide blocks, having a series of different length and spaced cutting slots would be available to the surgeon for use on a particular bone lesion. Also note, where the lesion has a non-uniform shape, a first cutting slot 106a can be used in connection with a third cutting slot, for example, 106c, as long as the same configuration of cuttings slots is used to prepare the allograft (see below).

Figure 1C:
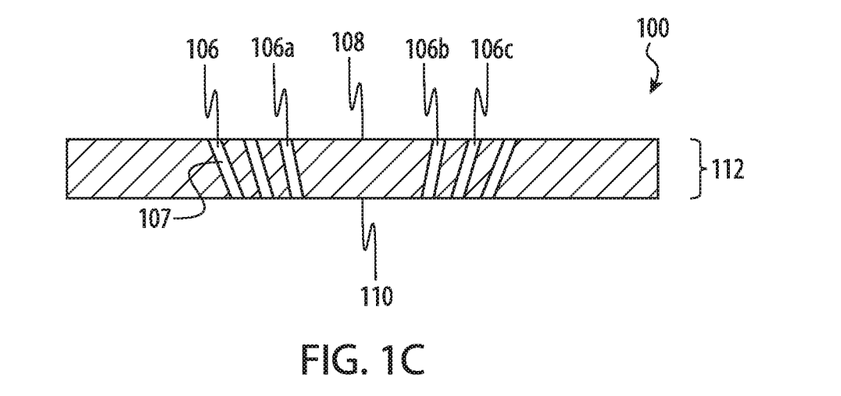
FIG. 1C is a cross-sectional view along line 1-1' of FIG. 1B.

FIG. 1C shows a cross-sectional view along line 1-1' of FIG. 1B. Recipient guide blocks 100 have a top surface 108 and an opposing bottom surface 110, with a uniform thickness (shown as 112) there between. Recipient guide block thickness 112 is sufficient to provide cutting slots 106 a surface for receiving a cutting tool and with enough surface area to guide the cutting tool through a recipient's lesion. In some aspects, the recipient guide block 100 is about 4 to 7 mm thick, and more typically about 4 mm to 6 mm thick, and most typically about 5 mm in uniform thickness. Cutting slots 106 off of the centerline are angled such that a surgeon has multiple options for preparing a lesion for implant. In one embodiment, a first angled cutting slot 106a is paired with a second angled cutting slot 106b for cutting out of a wedge shaped cavity from the site of lesion. As shown with the use of cutting slots 106a and 106b, angled cuts through the slots result in a wedge shaped cavity having a surface width of 20 mm, for example, and a depth of 25 mm, for example. Use of any two opposing cutting slots from the centerline 104 can be used, for example, 106a and 106c. Ends of the wedge are precision cut by the surgeon (or other health care professional) for release of the damaged bone (see dashed lines 109, FIG. 1B). Other cavity shapes are contemplated to be within the scope of the present embodiments, for preparation by the recipient guide block, as long as the allograft guide block has the same matching cutting parameters (see below).

Figure 2A:
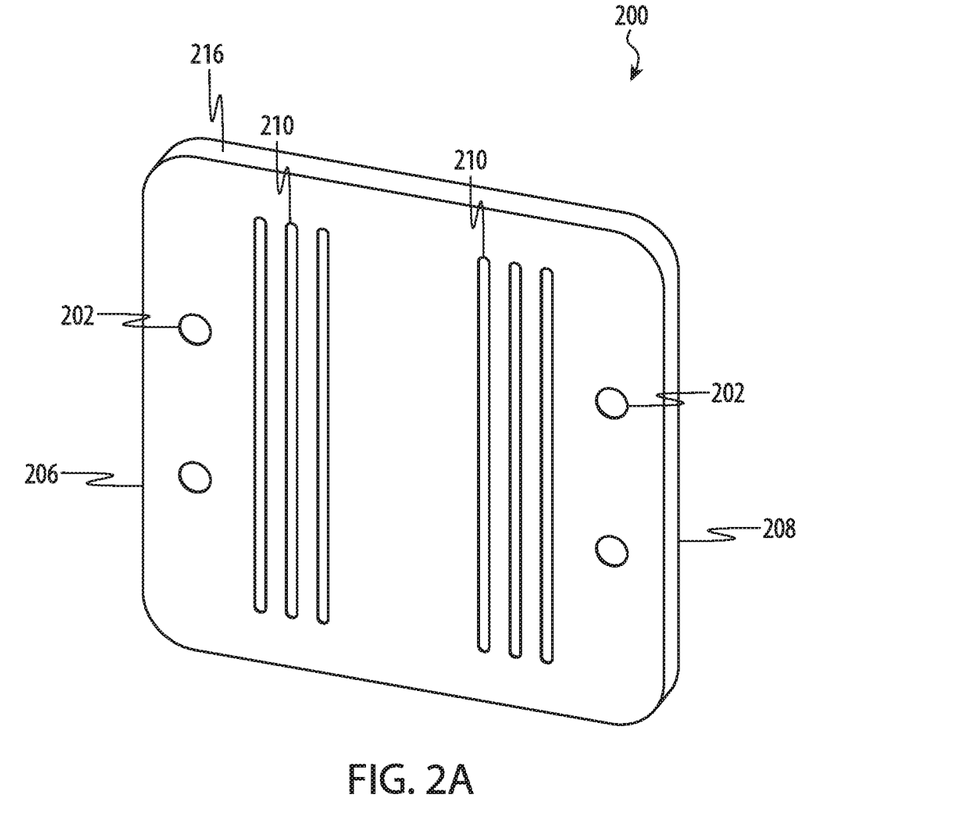
FIG. 2A schematically illustrates an allograft guide block in accordance with embodiments herein.
Figure 2B:
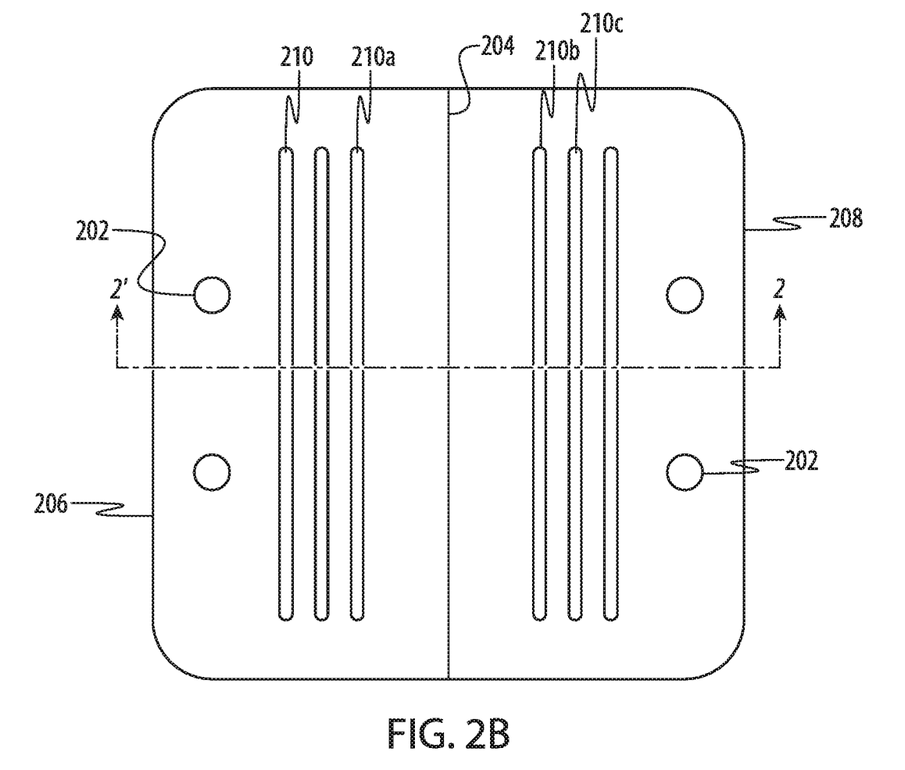
FIG. 2B is a top view of the allograft guide block in accordance with embodiments herein.

FIGS. 2A and 2B show a perspective and top view, respectively, of an allograft guide block 200 in accordance with embodiments herein. The allograft guide block 200 includes at least two holes for securing the guide block to the allograft source, and more typically at least four holes 202, two on either side of a centerline 204 (FIG. 2B), for securing the guide block 200 to the allograft or bone donor source. Referring to the schematic of FIGS. 2A and 2B, in one embodiment, two holes are equally spaced adjacent a first edge 206 of the guide block, and two holes equally spaced adjacent a second edge 208 of the guide block. In some cases, the first and second edges are opposite each other. Each hole is suitable for receipt of a "sidecar" pin or other like pin or screw. As discussed in greater detail below, in one embodiment, a surgeon or other like healthcare professional identifies and positions the allograft guide block on an allograft source and uses holes 202 to secure the block to the contoured surface of the allograft. Three or more paired cutting slots 210 are defined at proximal to distal intervals from the centerline, each cutting slot paired to a cutting slot positioned on the opposite side of the centerline. Cutting slots are matched from the centerline of the corresponding recipient guide block 100 with the exception that the cutting slots are offset by the width of the saw or other cutting instrument. So for example, where the cutting blade is 1 mm in thickness, the cutting slots can be positioned 11 mm on either side of the centerline, 16 mm off of the centerline, and 21 mm off of the centerline (to match the 10 mm, 15 mm, and 20 mm recipient guide block distances). Each cutting slot is roughly parallel to the centerline, and matched to the cutting slot pair on the recipient guide block, for example 106a and 106b with 210a and 210b. Where a lesion is removed from a humeral head, for example, using the recipient guide block cutting slots at 10 mm off of the centerline, the corresponding allograft guide block, having cutting slots at 11 mm, would be used to form the same sized allograft (and using a 1 mm thick cutting blade) as a cavity prepared in the recipient bone.

Figure 2C:
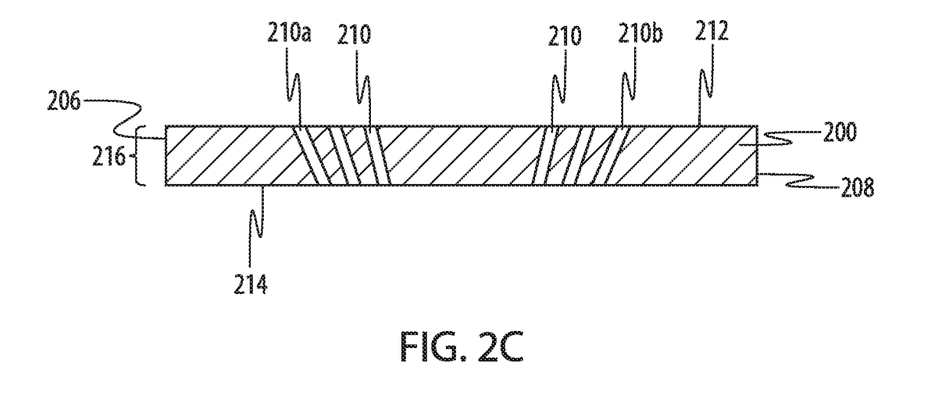
FIG. 2C is a cross-sectional view along line 2'-2 of FIG. 2B.

FIG. 2C shows a cross-sectional view along line 2-2' of FIG. 2B. Allograft guide blocks 200 have a top surface 212 and an opposing bottom surface 214, with a uniform thickness (show as 216) there between. Allograft guide block thickness is sufficient to provide cutting slots for receiving a cutting tool and with enough surface area to guide the cutting tool through an allograft source. In some aspects, the allograft guide block is about 4 to 7 mm thick, and more typically about 4 mm to 6 mm thick, and most typically about 5 mm in uniform thickness. Cutting slots off of the centerline are angled such that a surgeon has multiple options for preparing an implant. In one embodiment, a first angled cutting slot 210a is paired with a second angled cutting slot 210b for cutting out of a wedge shaped implant from the bone source. As noted above, the pair of cutting slots selected for use in the allograft guide block will match the cutting slots selected for use in the recipient guide block so as to result in allograft implants that fit within previously prepared cavities.

In typical embodiments, a surgeon or user would select a recipient guide block having similar, if not substantially the same, dimensions as an allograft guide block. Guide block thickness, cutting slot positioning and angle, cutting slot length, would all be matched to ensure that wedge shaped cavity preparation and wedge shaped allograft production be matched.

Figure 3:
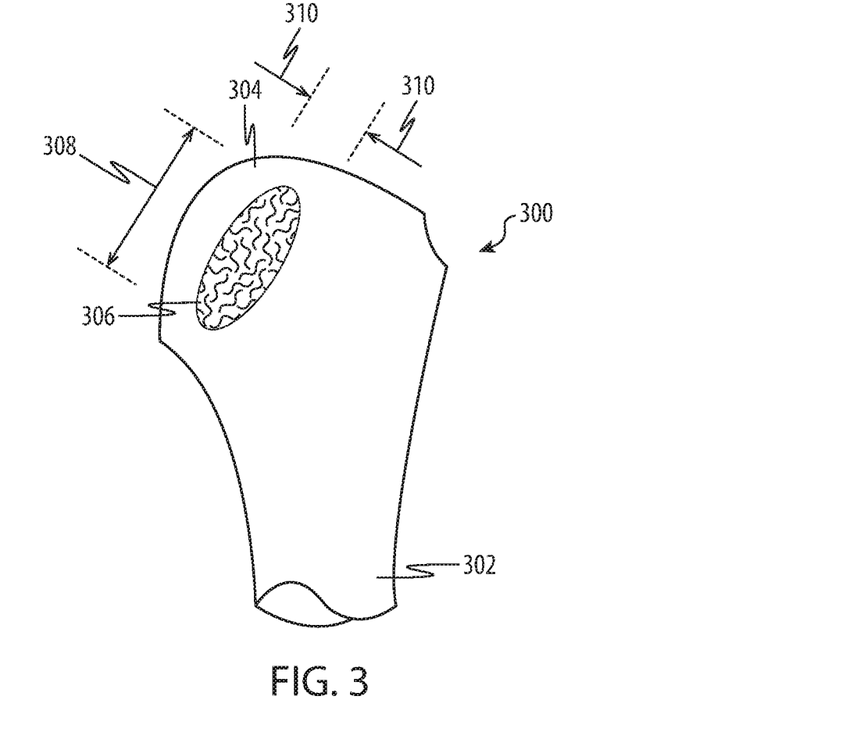
FIG. 3 schematically illustrates an illustrative bone defect of a human for treatment with embodiments described herein.

FIG. 3 illustrates a typical humeral head 300 with extending neck region 302 of the humerus (not shown). Humeral heads are rounded or hemispherical in shape 304. Humeral heads articulate with the glenoid cavity to form the glenohumeral joint or shoulder joint (not shown). Damage to the humeral head is typical during shoulder dislocation or sprain, upper arm fracture, or other like traumatic event. An illustrative bone lesion 306 is shown in the humeral head for repair in accordance with embodiments herein. As shown, the lesion can be extensive, affecting a significant portion of the head surface, with a length (arrow 308) and a width (arrows 310). Also note that most bone lesions are of an unusual shape and size that cannot be easily prepared by a surgeon or other health care provider in the absence of embodiments herein.

Figure 4:
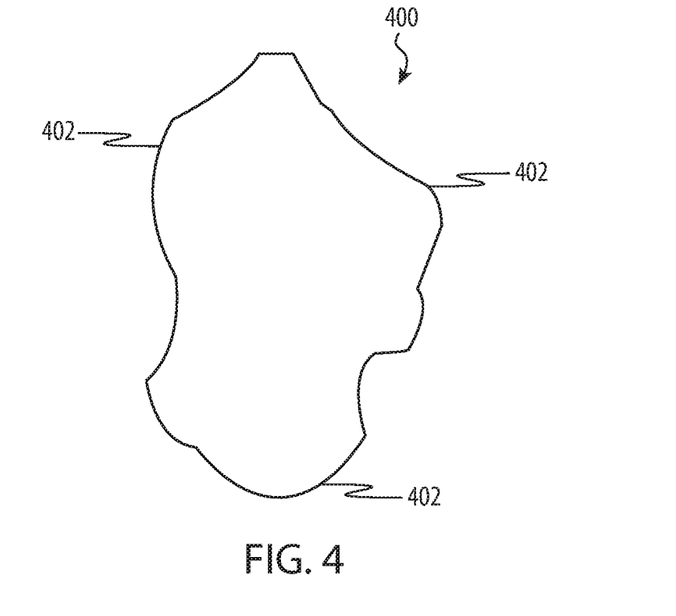
FIG. 4 is a top view of a talus bone for use as an illustrative allograft in accordance with embodiments herein.

Referring to FIG. 4, a top view of a talus bone 400 is shown. In the past, talus bone derived allografts have mostly been used for reconstruction of ankle joints, particularly where the talus was damaged. As recognized by the inventors herein, the talus bone has a similar radius of curvature 402 as does the humeral head 304, which makes it an excellent source for bone graft to the humeral head. Also disclosed herein, the talus bone has a surface mostly covered by articular cartilage, again making it an excellent source for use in the humeral head. This allows a surgeon to identify surface regions on the talus having an appropriate radius of curvature, and cartilage covering, such that the majority of the bone can be a potential allograft source. The talus bone is also an excellent source for implant due to its bone density and strength.

Figure 5:
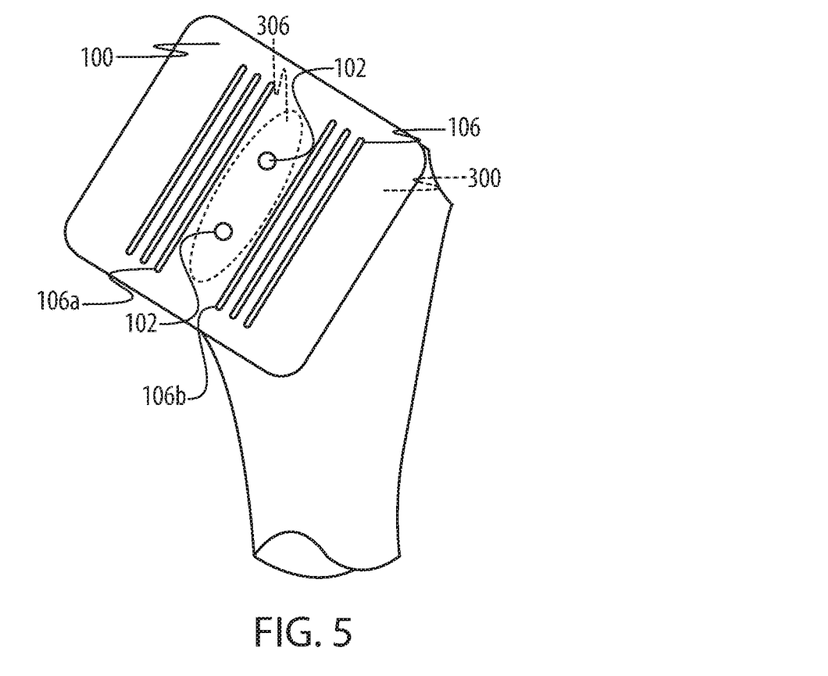
FIG. 5 schematically illustrates a recipient guide block attached to a bone lesion in accordance with embodiments herein.

As shown in FIG. 5, methods herein include locating a properly sized recipient guide block 100 for attachment to a lesion (shown as 306) on the humeral head 300. The recipient guide block 100 is secured directly to the humeral head through two openings 102 that align over the lesion. Alignment of the block is such that the cutting slots 106 roughly extend along either side of the lesion, for example 106a and 106b. Attachment to the recipient guide block within the lesion is acceptable given that the lesion will ultimately be removed using a cutting blade as discussed further below, i.e., damage to the lesion caused by attachment of the guide block is immaterial, as the damaged bone will be removed through use of the guide block.

Figure 6:
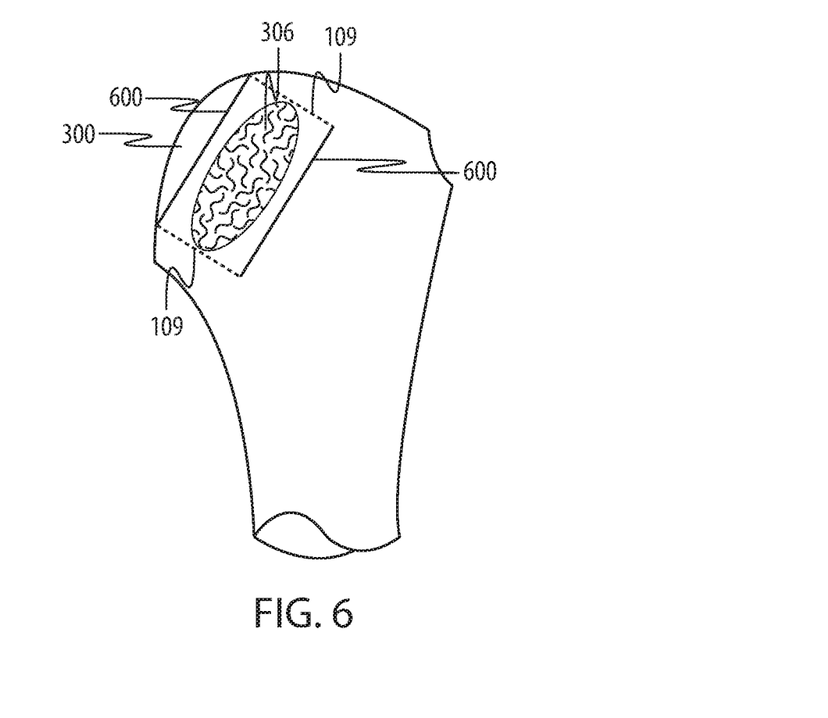
FIG. 6 schematically illustrates a bone lesion having vertical cuts along the lesion as guided by the recipient guide block.

Referring to FIG. 6, a surgeon or other health care provider makes angled cuts 600 on either side of the lesion 306 using a cutting blade (typically a saw or jigsaw) received in the recipient guide block cutting slots (FIG. 5, 106). Angled cuts 600 are typically sufficiently deep to intersect along an edge at a sufficient depth to remove the damaged bone (see FIG. 1B). The recipient guide block is then removed off of the humeral head. The surgeon may then cut along lines 109 to expose a cavity having cuts as described above.

Figure 7:
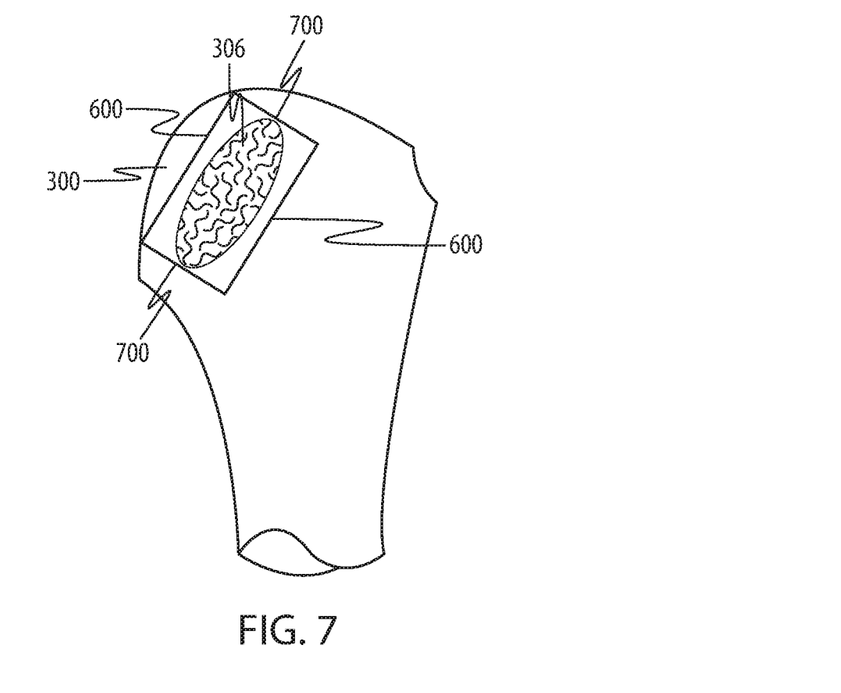
FIG. 7 schematically illustrates a bone lesion having cuts input into the bone for removal of the lesion and preparation of a predetermined sized cavity in accordance with embodiments herein.
Figure 8:
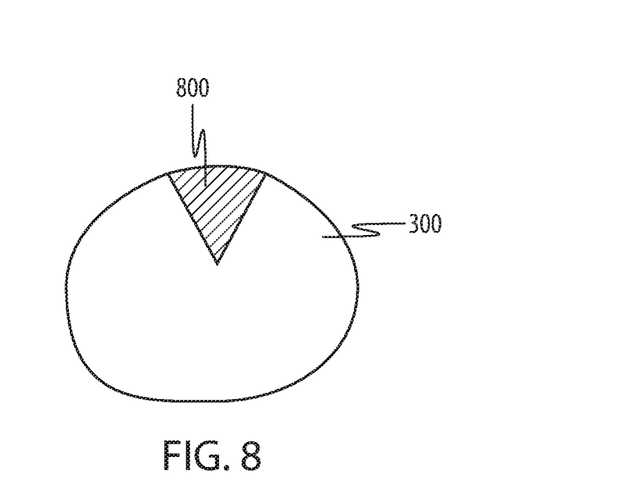
FIG. 8 is a cross-sectional view along an illustrative bone defect showing the wedge shaped bone to be removed from the lesion site in accordance with embodiments herein.

As shown in FIG. 7, two vertical cuts 700 are then made by the surgeon, along line 109, on either end of the lesion to form a wedge of bone tissue for removal from the humeral head. The wedge of tissue for removal has a known volume that corresponds to the particular cutting slots used by the surgeon 600 and 700. A schematic cross-sectional view of one such wedge 800 is shown in a humeral head, FIG. 8. Note the predictability of the cavity volume and size.

Figure 9:
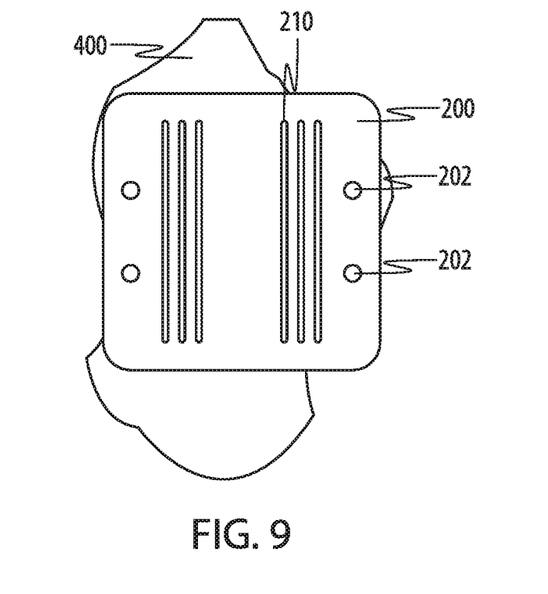
FIG. 9 schematically illustrates an allograft guide block attached to a bone implant source in accordance with embodiments herein.
Figure 10:
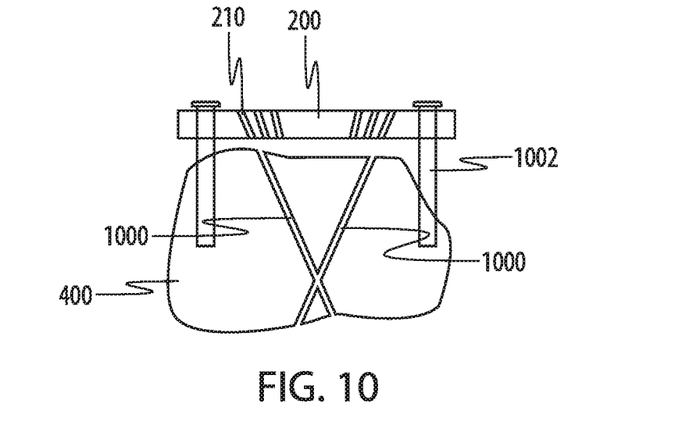
FIG. 10 is a cross-sectional view of the wedge shaped allograft prepared according to embodiments herein.
Figure 11:
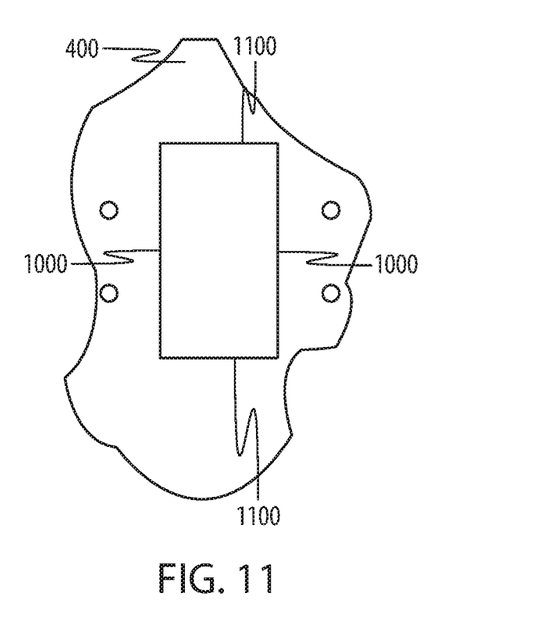
FIG. 11 schematically illustrates a bone source having cuts input into the bone for preparation of a predetermined sized implant in accordance with embodiments herein.

An allograft guide block 200 having appropriate dimensions (matching the recipient guide block) is shown directly attached to a talus in FIG. 9. The allograft guide block 200 is directly attached to a surface having the estimated radius of curvature necessary for the humeral head implant. The estimated radius is identified by the surgeon. A series of four sidecar pins (see FIG. 10, 1002) are received in the allograft guide block 200 to secure the block to the talus surface. Unlike the recipient guide block, the attachment points to the talus bone are outside the graft area (away from the centerline), so as to not form a defect within the allograft. Cutting slots 210, having the additional width of the cutting blade incorporated, are matched to the cutting slots on the recipient guide block. As shown in FIG. 10, two angled cuts 1000 are made into the talus bone 400 through the cutting slots, using the same or a similar tool as used to cut out the humeral head lesion. Direct attachment of the allograft guide block to the talus surface allows preparation of a wedge having the same dimensions as is now present in the humeral head. A top view showing the talus bone with implant cuts 1000 and attachment points is shown in FIG. 11. After removal of the allograft guide block from the talus, two cuts 1100 are made by the surgeon to prepare the sized wedge shaped allograft for use in the humeral head cavity. By using the allograft guide block, the surgeon is thus able to form an allograft that roughly matches the cavity prepared in the humeral head.

Figure 12:
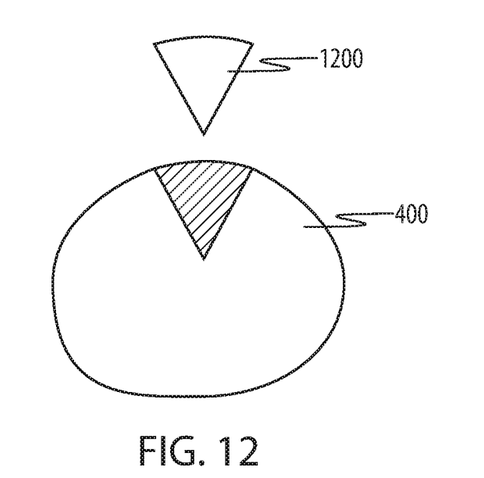
FIG. 12 schematically shows a wedge shaped implant in accordance with embodiments herein.
Figure 13:
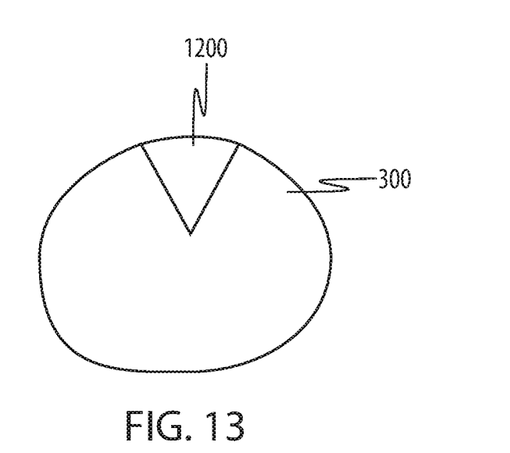
FIG. 13 schematically illustrates placement of the wedge shaped implant into a matching cavity in accordance with embodiments herein.

FIGS. 12 and 13 show that the wedge shaped allograft can be removed from the talus (FIG. 12) and positioned within the previously prepared cavity of the humeral head (FIG. 13). In some aspects, the surgeon may be required to modify the size of the allograft by removing layers or shaving layers of material from the allograft until the implant snugly fits or mates with the cavity. In addition, a surgeon may wish to shave surface contour off of the implant to mate the implant contour with the articular surface of the recipient humeral head.

In other embodiments, guide blocks can be sizable based on the gender of the recipient, male or female, or based on the size of the bone lesion. So for example, a number of different sized guide blocks can be provided to a surgeon to choose from based on whether the patient is male or female, or based on the percent of the glenoid surface needing to be repaired, i.e., size and shape of the defect.

In another embodiment, as is shown in greater detail below, allograft guide blocks can also be configured to be secured to a bone donor source using a scaffold fixture, for example, a vice and movable post configuration.

Figure 14:
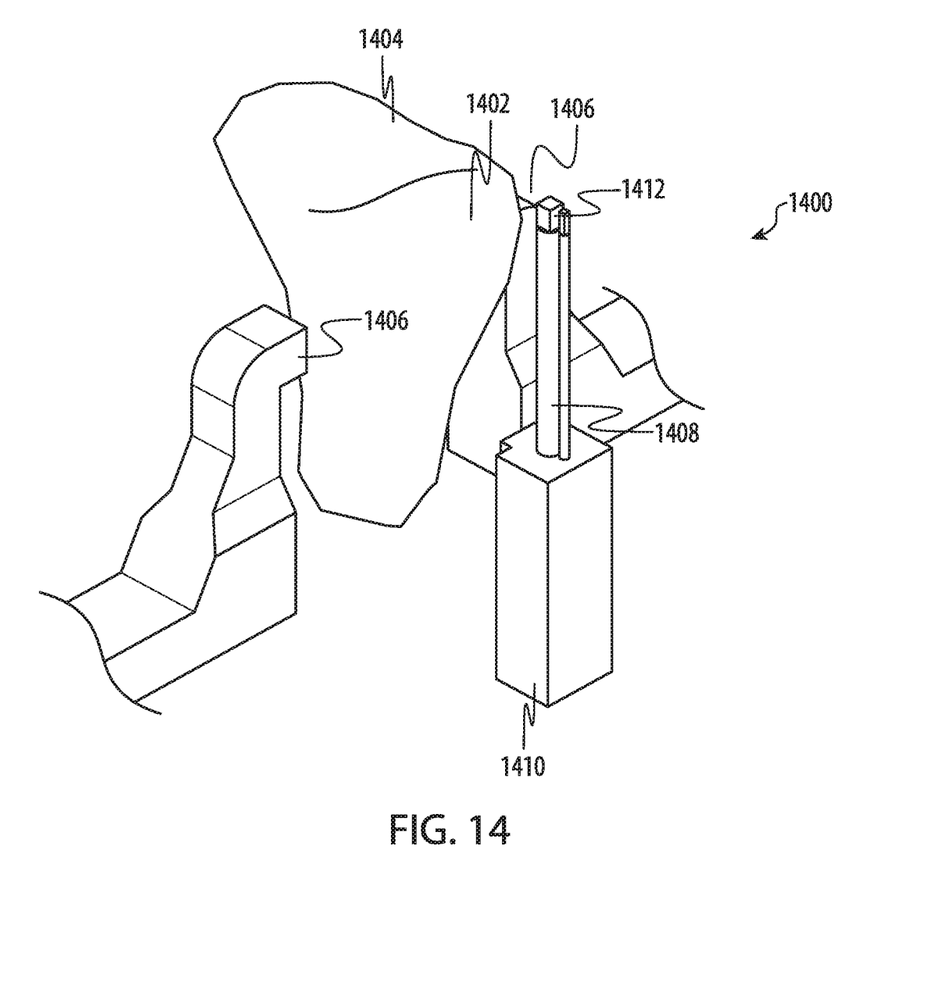
FIG. 14 schematically illustrates a scaffolding fixture for securing an allograft source for allograft production, and having a post for use with an allograft guide block in accordance to embodiments herein.

FIG. 14 shows a scaffolding fixture 1400 and allograft donor bone 1402 secured from movement. The bone 1402 is positioned to present an allograft surface 1404, with appropriate surface contour, for harvest, using the embodiments herein. Other securing means beyond a vice 1406 are envisioned to be within the scope of the present disclosure, but a vice 1406 is used as illustrative.

A movable post 1408, relative to the secured allograft donor bone 1402, is positioned in relation to the secured donor bone. The post 1402 extends upwardly from a base 1410 to a distance where the top end 1412 of the post exceeds the top surface of a donor bone, e.g., talus or humeral head. This juxtaposition allows for a guide block (see FIG. 15) to be attached to the post 1408 and positioned over the donor bone 1402/1404. In some aspects, the post 1408 is cylindrical in cross-section, but it can be configured using any desired cross-sectional shape, i.e., oval, square, rectangular, octagonal, etc. The top end 1412 of the post 1408 defines a unique attachment point for interaction with an allograft guide block. The post 1408 itself can be raised or lowered in relation to the secured donor bone 1402, such that the top end 1412 is always configured to be positionable in relation to the contour surface 1404 of the donor bone.

Figure 15:
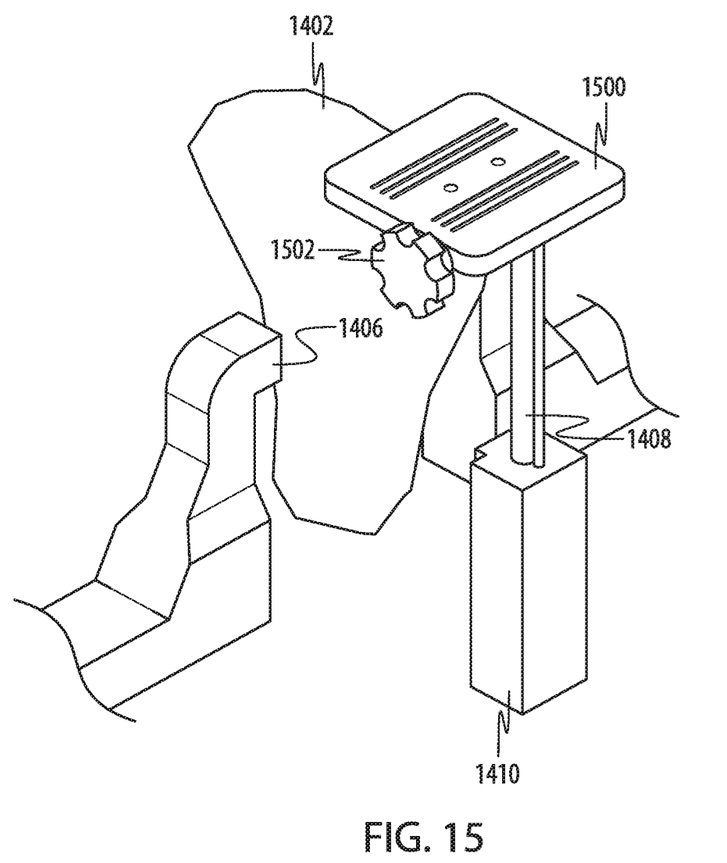
FIG. 15 schematically illustrates the scaffolding fixture in FIG. 14, having a post, and further with an allograft guide block operatively attached to a top end of the post in accordance with embodiments herein.

FIG. 15 shows allograft guide block 1500 attached to the top end (not shown) of the post 1408. The allograft guide block 1500 defines a mounting slot (not shown), for example, a keyhole shaped slot in the bottom surface (not shown) of the guide block 1500. The top end of the post 1408 would, in this case, define a matching key shape to attach to and mount via the keyhole shaped slot in the bottom of the guide block. The mounting of the guide block to the top end of the post can be through other attachment means, and at alternative locations, for example the edge of the guide block to a surface of the post. In some aspects, the post 1408 can be rotated within its base, so that the attached allograft guide block 1500 can be extended over the target donor bone 1402 and donor bone surface. In addition, the mounting engagement between the allograft guide block 1500 and post 1408 can also be configured to allow movement of the guide block 1500 in an angled relation to the surface of the donor bone 1402. Once an allograft guide block 1500 is positioned over the appropriate surface of donor bone, the block can be secured in place (using a cam or other positional device 1502), and the surgeon can cut out the correctly sized allograft.

Although not shown, concave shaped guide blocks can be substituted for flat shaped guide blocks in embodiments herein. These blocks can be directly attached to the recipient and donor bones, and can be used via the scaffolding embodiments. Concave guide blocks can be prepared and matched together based on a number of related curvatures.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

What is claimed is:

1. A instrumentation set for restoration of a bone lesion, comprising:
    a recipient guide block defining:
        a top surface;
        a bottom surface opposite to the top surface;
        a first guide feature that extends from the top surface to the bottom surface along a first plane that is inclined with respect to the bottom surface;
        a second guide feature that extends from the top surface to the bottom surface along a second plane that is inclined with respect to the bottom surface, the second plane intersecting the first plane at a location below the bottom surface; and
        a set of holes positioned between the first guide feature and the second guide feature along a central portion of the recipient guide block, the set of holes configured to secure the recipient guide block against a surface of the bone lesion, the first and second guide features configured to guide a user in the preparation of a wedge-shaped cavity,
    wherein the bottom surface of the recipient guide block has a concave curvature that is configured to correspond to a convex curvature of an exterior surface of the bone lesion; and
    an allograft guide block configured to be secured against a surface of a bone source and guide the user to prepare a wedge-shaped allograft;
    wherein the wedge-shaped allograft is prepared so as to be secured into the wedge-shaped cavity.

2. The instrumentation set for restoration of the bone lesion as recited in claim 1, wherein the recipient guide block is configured to directly attach to the bone lesion.

3. The instrumentation set for restoration of the bone lesion as recited in claim 1, wherein the allograft guide block is configured to directly attach to the bone source.

4. The instrumentation set for restoration of the bone lesion as recited in claim 1, wherein the allograft guide block is secured by a scaffold fixture to be positioned against the surface of the bone source.

5. The instrumentation set for restoration of the bone lesion as recited in claim 1, wherein the bone lesion is in a humeral head of a patient.

6. The instrumentation set for restoration of the bone lesion as recited in claim 5, wherein the bone source is a talus bone.

7. The instrumentation set for restoration of the bone lesion as recited in claim 5, wherein the bone source is the humeral head.

8. The instrumentation set for restoration of the bone lesion as recited in claim 1, wherein the recipient guide block defines a first uniform thickness extending between the top surface and the bottom surface, and the distance between the top surface and the bottom surface is from about 4 mm to about 7 mm.

9. The instrumentation set for restoration of the bone lesion as recited in claim 8, wherein the recipient guide block has a centerline; and the set of holes of the recipient guide block are positioned along the centerline and are configured to accept screws or pins to directly attach the recipient guide block into the bone lesion.

10. The instrumentation set for restoration of the bone lesion as recited in claim 9, wherein: the first guide feature comprises a first cutting slot at a first distance from the centerline, and the second guide feature comprises a second cutting slot at a second distance from the centerline, the first and second distances being substantially equal and on opposite sides of the centerline; and wherein the first cutting slot and second cutting slot are configured to allow the user to make angled cuts along either side of the bone lesion.

11. The instrumentation set for restoration of the bone lesion as recited in claim 1, wherein a first uniform thickness extends between the top surface and the bottom surface, and the distance between the top surface and the bottom surface is from about 4 mm to about 7 mm.

12. The instrumentation set for restoration of the bone lesion as recited in claim 11, wherein the allograft guide block has a centerline; and the allograft guide block has at least four holes, at least two holes on a first side of the centerline and at least two holes on an opposing side of the centerline, the at least four holes configured to accept screws or pins to directly attach the allograft guide block on the bone source;

wherein the at least four holes do not overlap the wedge-shaped allograft.

13. The instrumentation set for restoration of the bone lesion as recited in claim 1, wherein a first radius of contour of an exterior surface of the allograft is substantially the same as a second radius of contour of an exterior surface of the bone lesion.

14. A method, comprising:
obtaining a donor bone as an allograft source;
securing a recipient guide block against a surface of a recipient bone having a bone lesion using a set of attachment holes positioned along a central portion of the recipient guide block, the recipient guide block having a concave curvature that is configured to correspond to a convex curvature of the recipient bone,
cutting a wedge-shaped cavity from the surface of the bone lesion using the recipient guide block, the cutting comprising:
making a first cut using a first guide feature that is inclined with respect to a bottom surface of the recipient guide block; and
making a second cut using a second guide feature that is inclined with respect to the bottom surface of the recipient guide block, the first and second cuts intersecting in a region of the recipient bone that is positioned below the bone lesion;
securing an allograft guide block against a surface of the donor bone to obtain a wedge-shaped implant that has a first shape that corresponds to a second shape of the wedge-shaped cavity, the allograft guide block defining at least one pair of included guide features that are used to obtain the wedge-shaped implant; and
securing the wedge-shaped implant into the wedge-shaped cavity.

15. The method of claim 14, wherein: a contour of an exterior surface of the wedge-shaped implant has a first radius that corresponds to a second radius of an exterior surface of the bone lesion.

16. The method of claim 14, wherein:
the securing of the allograft guide block to the donor bone is through the use of at least 4 sidecar pins.

17. The method of claim 14, wherein:
the first cut is performed by using the first guide feature to guide a cutting blade along a first cutting path; and
the second cut is performed by using the second guide feature to guide the cutting blade along a second cutting path.

18. The method of claim 17, wherein:
the first guide feature is parallel to the second guide feature; and
the first guide feature is separated from the second guide feature by at least 20 mm.

19. A kit for surgically repairing a lesion in a humeral head, comprising:
a recipient guide block defining:
a top surface;
a bottom surface opposite to the top surface, the bottom surface having a concave curvature that is configured to correspond to a convex curvature of the humeral head;
a first guide feature that extends from the top surface to the bottom surface along a first incline with respect to the bottom surface; and
a second guide feature that extends from the top surface to the bottom surface along a second incline with respect to the bottom surface, the first and second guide features configured to guide a cutting tool in creation of a wedge-shaped cavity in the humeral head; and
a set of holes positioned between the first guide feature and the second guide feature along a central portion of the recipient guide block, the set of holes configured to secure the recipient guide block to the humeral head configured to be secured directly against the lesion and to guide preparation of a wedge-shaped cavity at the lesion;
an allograft guide block configured to be secured directly against an allograft source and to guide preparation of a wedge-shaped implant for positioning in the wedge-shaped cavity; and
instructions on how to utilize the recipient guide block and the allograft guide block to repair the lesion in the humeral head.

20. The kit of claim 19, further comprising:
pins or screws for use in directly securing the recipient guide block to the lesion and
sidecar pins for use in directly securing the allograft guide block to the allograft source.

21. The kit of claim 20, wherein the allograft guide block is configured to be secured directly against a talus bone as the allograft source.

* * * * *